(12) United States Patent
Barrett

(10) Patent No.: US 8,399,495 B2
(45) Date of Patent: Mar. 19, 2013

(54) TALARAZOLE METABOLITES

(75) Inventor: Debra Barrett, Princeton, NJ (US)

(73) Assignee: Stiefel Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 13/476,216

(22) Filed: May 21, 2012

(65) Prior Publication Data

US 2012/0283204 A1 Nov. 8, 2012

Related U.S. Application Data

(63) Continuation of application No. 12/311,862, filed as application No. PCT/US2007/081685 on Oct. 17, 2007, now Pat. No. 8,188,124.

(60) Provisional application No. 60/851,989, filed on Oct. 17, 2006.

(51) Int. Cl.
| | |
|---|---|
| *A01N 43/64* | (2006.01) |
| *A01N 43/82* | (2006.01) |
| *A01N 43/78* | (2006.01) |
| *A61K 31/41* | (2006.01) |
| *A61K 31/425* | (2006.01) |

(52) U.S. Cl. ........ 514/359; 514/360; 514/365; 514/366; 514/383

(58) Field of Classification Search .......... 514/359, 514/360, 365, 366, 370, 383
See application file for complete search history.

(56) References Cited

U.S. PATENT DOCUMENTS

| | | |
|---|---|---|
| 6,124,330 A | 9/2000 | Venet et al. |
| 6,486,187 B1 | 11/2002 | Venet et al. |
| 6,608,070 B1 | 8/2003 | Nakao et al. |
| 6,833,375 B2 | 12/2004 | Venet et al. |
| 2006/0160870 A1 | 7/2006 | Majka et al. |
| 2006/0189549 A1 | 8/2006 | Ni et al. |
| 2006/0189627 A1 | 8/2006 | Laird et al. |
| 2006/0205945 A1 | 9/2006 | Kath et al. |

OTHER PUBLICATIONS

Gu, Zhe-Ming, et al. Drug Met. Reviews, 38(Supp. 2): 176 (2006).

*Primary Examiner* — Yong Chong
(74) *Attorney, Agent, or Firm* — Dara L. Dinner; Theodore R. Furman

(57) ABSTRACT

Novel metabolites of talarazole of formula (I) have been isolated and characterized, wherein R=H, OH, $OSO_3H$ or O-gly; $R_1$, =H, OH, $OSO_3H$, O-gly or =O; and gly=a glucuronate, or a pharmaceutically acceptable salt thereof. These compounds are targeted for the treatment of various skin-, hair- and nail-associated disorders.

16 Claims, 1 Drawing Sheet

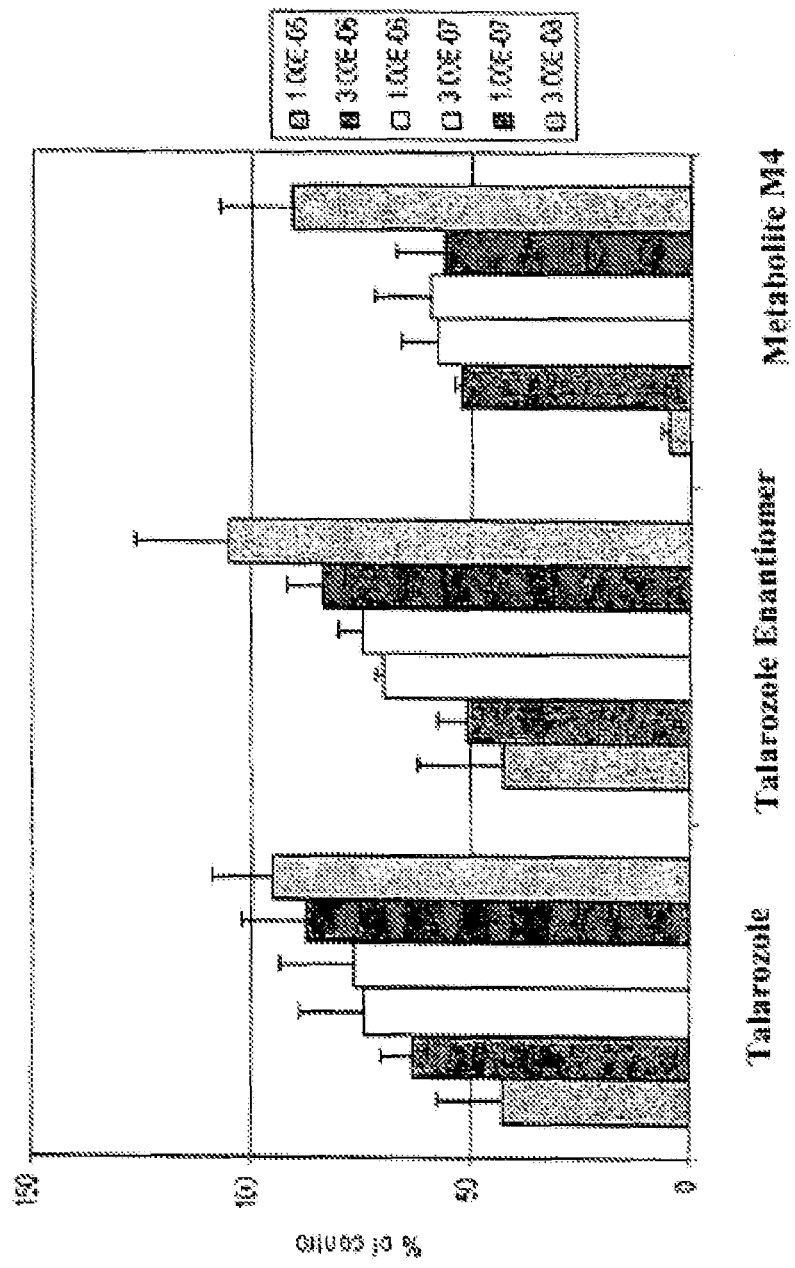

TALARAZOLE METABOLITES

This application is a continuation of application Ser. No. 12/311,862, filed 29 Jun. 2009 now U.S. Pat. No. 8,188,124, which is a §371 of International Application No. PCT/US2007/081685, filed 17 Oct. 2007, which claims the benefit of U.S. Provisional Application No. 60/851,989, filed 17 Oct. 2006, which are incorporated herein in their entireties.

FIELD OF THE INVENTION

This application is directed to novel metabolites of talarozole (formerly referred to as rambazole). The application is also directed to the use of these metabolites for the treatment of various skin-, hair- and nail-associated disorders.

BACKGROUND OF THE INVENTION

Talarozole ((R)—N-[4-[2-ethyl-1-(1H-1,2,4-triazole-1-yl)butyl]phenyl]-2-benzothiazolamine) (formerly referred to as rambazole) is a novel enantiomerically pure retinoic acid metabolism-blocking agent (RAMBA). In preclinical in vitro and animal studies, topical talarozole has demonstrated potential effectiveness in the treatment of psoriasis, acne and photo-damage. Oral talarozole is being developed for the treatment of moderate to severe psoriasis and potentially acne. See, e.g., U.S. Pat. Nos. 6,833,375; 6,486,187 and 6,124,330, each of which is incorporated by reference in its entirety. Given talarozole's promise as a potent therapeutic agent, its metabolism in selected animal species was investigated and novel talarozole metabolites were isolated and characterized. Select metabolites were evaluated as therapeutic agents, especially in the treatment of keratinization-associated disorders.

SUMMARY OF THE INVENTION

An aspect of the invention is a novel isolated metabolite of talarozole as represented by Formula I.

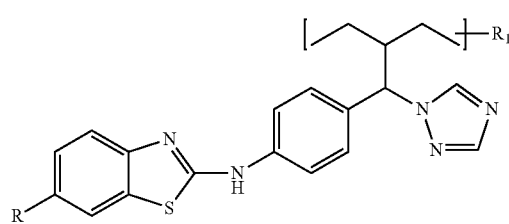

Formula I wherein R=H, OH, OSO₃H or O-gly; R₁=H, OH, OSO₃H, O-gly or =O; and gly=a glucuronate, or a pharmaceutically acceptable salt thereof, with the proviso that when R=H, R₁ cannot also be H.

Another aspect of the invention is a compound selected from the group consisting of

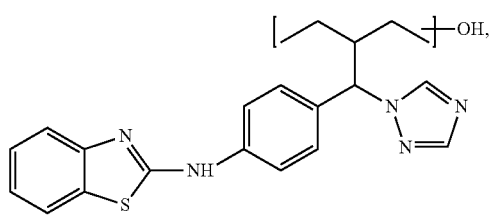

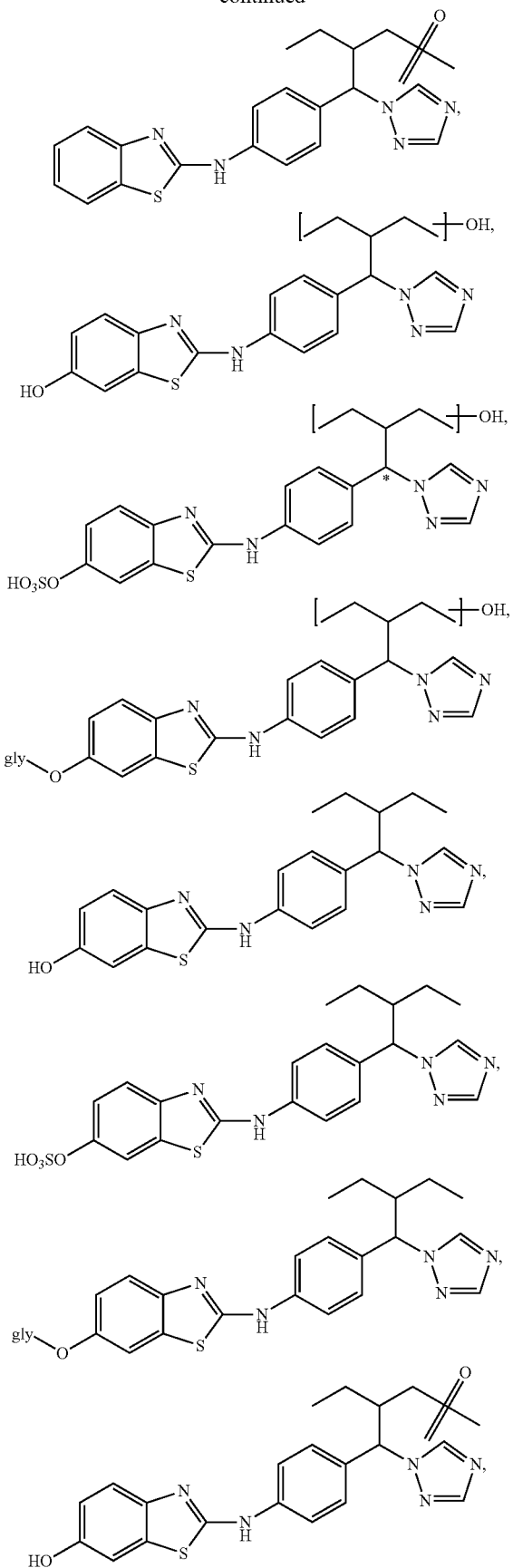

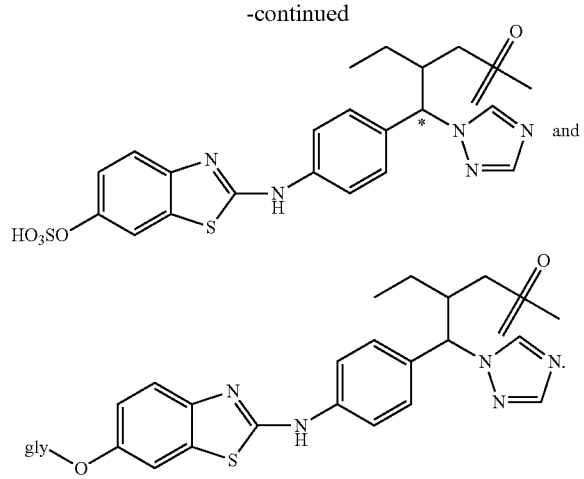

Another aspect of the invention is the treatment of keratinization-associated disorders (e.g., various skin-, hair- and nail-associated disorders) in a warm-blooded mammal in need thereof, comprising administering to the mammal an effective amount of a talarozole metabolite of Formula I.

Another aspect of the invention is a pharmaceutical composition comprising a novel metabolite of talarozole and a diluent or carrier.

BRIEF DESCRIPTION OF DRAWINGS

FIG. 1 shows a comparison of the various talarozole metabolites across selected animal species.

DETAILED DESCRIPTION

Pharmaceutically acceptable salts of the metabolites of the invention include the conventional non-toxic salts that are known in the art and which are formed by the addition of inorganic or organic acids or bases. Examples of acid addition salts include, but are not limited to, acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

It is well known in the art that hydroxyl groups on chemical compounds are subject to in vivo glycosylation. Selected isolated metabolites of talarozole that contain one or more hydroxyl groups are evidence of this process occurring in the mammals studied, including humans. In an exemplary embodiment, the glycoside is a glucuronide formed by the reaction between glucuronic acid and one or more hydroxyl groups present in the metabolite.

In addition to carriers, the pharmaceutical compositions of the invention may also include stabilizers and preservatives. For examples of typical carriers, stabilizers and adjuvants known to those of skill in the art, see Remington: The Science and Practice of Pharmacy, 21$^{st}$ ed. (Lippincott, Williams & Wilkins (2005)).

The novel metabolites of this invention may be administered alone or preferably as a pharmaceutical formulation comprising the metabolite together with at least one pharmaceutically acceptable carrier. Optionally, other therapies known to those of skill in the art may be combined with the administration of the metabolites of the invention. More than one metabolite may be present in a single composition.

The metabolites of the invention are potential biological process modulators that likely impact cell proliferation and differentiation (e.g., keratinocytes, fibroblasts, endothelial cells, sebocytes), immune function (e.g., hemapoeic cells) and may be used in the treatment of skin-, hair- and nail-disorders such as, but not limited to, psoriasis, acne, actinic keratosis, eczema, rosacea, ichthyosis, alopecia and photo-damaged skin. Further, the metabolites of the invention may be use in the treatment of cancer, such as prostate cancer, basal and squamous cell carcinomas and melanoma. This invention includes methods for the treatment of keratinization disorders in a mammal, including a human, comprising administering to said mammal an amount of the compound of the invention or a pharmaceutical composition comprising or consisting of the compound of the invention, that is effective in inhibiting or arresting IP-10 dependent growth of abnormally proliferating epidermal cells, such as keratinocytes, without the addition of other therapeutic agents. In one embodiment of this method, the abnormal cell growth is a type of carcinoma, including but not limited to, basal cell carcinoma, squamous cell carcinoma. In another embodiment the abnormal cell growth is a type of melanoma.

An "effective amount" is an amount sufficient to effect beneficial or desired results. For example, a therapeutic amount is one that achieves the desired therapeutic effect. In an exemplary embodiment, the daily dose may range from about 0.005 to about 5 mg/kg. This amount may be the same or different from a prophylactically effective amount, which is an amount necessary to prevent the onset of disease or disease symptoms. An effective amount can be administered in one or more administrations, applications or dosages.

Methods of determining the most effective means and dosage of administration are well known to those of skill in the art and will vary with the composition used for therapy, the purpose of the therapy, the target cell being treated and the subject being treated. Single or multiple administrations can be carried out with the dose level and pattern being selected by the treating physician.

In an exemplary embodiment, the recipient of the metabolites of the invention is a warm-blooded mammal, preferably a human.

Pharmaceutical compositions containing the metabolites of the invention can be administered by any suitable route, including oral, rectal, intranasal, topical (including transdermal, aerosol, buccal and sublingual), parenteral (including subcutaneous, intramuscular, intravenous), intraperitoneal and pulmonary. It will be appreciated that the preferred route will vary with the condition and age of the recipient, and the disease being treated.

EXPERIMENTAL

Mouse, rat, dog and human were the species used for the safety evaluations of talarozole. More specifically, the disposition of $^{14}$C-labeled talarozole was examined in mice, rats, dogs and humans after oral administration to provide information regarding the absorption, metabolism and excretion of talarozole.

Example 1

Analysis of Talarozole Metabolites

Male and female CD-1 mice (19-29 g, n=3/sex/timepoint for blood sampling, n=3/sex for mass balance), Sprague Dawley rats (0.205-0.237 kg, n=3/sex/timepoint for blood sampling, n=3/sex for mass balance) and beagle dogs (7-12 kg, n=3) were given a single oral dose of $^{14}$C-labeled talarozole in 20% hydroxyl propyl B-cyclodextrin at 5 mg/kg. Healthy human male volunteers (76.6-107.9 kg, n=5) were dosed with a single oral dose of 4 mg $^{14}$C-labeled rambazole in ethanol. Blood samples were collected at selected timepoints after dosing and plasma was prepared. Urine and feces were collected for 2, 7 and 8 days. For the human study, up to 288 hours post-dose and semen samples were obtained 2 and 4 hours post-dose. Radioactivity in various matrices were measured by liquid scintillation counting (LSC). Select plasma, urine and fecal samples were subjected to metabolite radioprofiling and characterization, and in the human study, semen samples. Metabolite radioprofiling was accomplished using HPLC with fraction collection followed by solid scintillation counting (Packard TopCount—see representative HPLC run data below). Radioactivity peaks were integrated and the percent distribution of individual metabolites in each sample was determined. Metabolite characterization and identification were accomplished by LC/MS (Finnigan MAT LCQ in positive or negative ESI mode) in conjunction with an appropriate radioactive monitor (RAM). For all species, plasma, urine and fecal samples were pooled across animals and analyzed. Plasma was analyzed at several time-points out to 24 hours. Urine was analyzed over one time-interval (0-24 hours for mouse, 0-48 hours for rat, 0-72 hours for dog, and for in the human study, 0-12, 12-24, 24-48, 0-48 hours. Feces was analyzed over 2-3 time intervals (0-24 and 24-48 hours for mouse and rat; 0-24, 24-48, and 48-72 hours for male dogs; and 24-48, 48-72, and 72-96 hours for female dogs). In the human study, feces were analyzed for 0-48, 48-96, 96-144, 144-192, 192-288, 0-144, 144-288 and 0-288 hours. PK parameters for $^{14}$C-labeled talarozole radioactivity was determined from the mean (mouse and rat) or individual (dog and human) plasma concentration versus time data. PK parameter values were determined by non-compartmental methods using WinNonlin™.

HPLC data for separations described in Example 1:
LC system: Waters 2695 Separations Module
Analytic column: C18 column, 4.6×150 mm, 3 µm
Flow rate: 1.0 mL/min
Mobile phase A: 2% HCOOH in H$_2$O (pH 3.2)
Mobile phase B: CH$_3$CN
Gradient:

| (min) | (mL/min) | A (%) | B (%) |
|---|---|---|---|
| 0 | 0.7 | 100 | 0 |
| 3 | 0.7 | 100 | 0 |
| 28 | 0.7 | 75 | 25 |
| 48 | 0.7 | 65 | 35 |
| 78 | 0.7 | 30 | 70 |
| 83 | 0.7 | 0 | 100 |
| 88 | 0.7 | 0 | 100 |
| 90 | 0.7 | 100 | 0 |
| 105 | 0.7 | 100 | 0 |

Example 2

Effects on Epithelial Differentiation in Rat Vagina: Inhibition of Vaginal Keratinization Induced by Estrogenic Treatment in Ovariectomized Rats by Oral Administration of Talarozole Metabolite M4

This animal model is based on the observation that retinoic acid (RA) suppresses the keratinization process in the stratified squamous epithelium of the vagina induced by estrogenic treatment in ovariectomized rats (Sietsema & DeLuca, 1982; Geiger & Weiser, 1989). ED$_{50}$-value for complete suppression (keratinization score=0) was 1.0 mg/kg/day for talarozole whereas ED$_{50}$-value for RA was 5.1 mg/kg/day. Oral administration of M4 during 3 days inhibited vaginal keratinization induced by estrogenic treatment in ovariectomized rats in a dose-dependent manner. ED$_{50}$-value for complete suppression (keratinization score=0) by M4 was 1.2 mg/kg/day.

Example 3

Talarozole Metabolites for Suppression of IP-10 Production by IFNγ-Activated Human Epidermal Keratinocytes IP-10, a member of the CXC subfamily of chemokines, attracts T-lymphocytes and natural killer cells. IP-10 is upregulated in, for example, psoriasis. In particular, epidermal keratinocytes of psoriatic lesions express elevated levels of IP-10. Suppression of IP-10 expression by activated keratinocytes may represent a novel target for therapeutic intervention of inflammatory skin disorders. Talarozole, its enantiomer and metabolite M4 were observed to down regulate dose-dependently IP-10 expression as shown in FIG. 1.

Results and Discussion
Pharmacokinetics of Radioactivity
PK parameters for $^{14}$C-labeled talarozole are shown in Table 1.

TABLE 1

Mean Pharmacokinetic Parameters of $^{14}$C-labeled Talarozole Equivalents in Plasma

| Species (0-t) | Sex | Cmax (ng equiv/g) | Tmax (hours) | $t_{1/2}$ (hours) | AUC$_{0-t}$ (hr-ng equiv/g) | AUC$_{0-\infty}$ (hr-ng equiv/g) |
|---|---|---|---|---|---|---|
| Mouse (0-48 h) | Male | 2633 | 3.0 | 7.6 | 10215 | 10276 |
| | Female | 1839 | 1.0 | 12.4 | 6632 | 6767 |
| Rat (0-48 h) | Male | 1130 | 2.0 | 17.4 | 6720 | 6960 |
| | Female | 838 | 4.0 | 14.8 | 7670 | 7810 |
| Dog (0-168 h) | Male | 2533 | 0.67 | 55.7 | 19555 | 19970 |
| | Female | 2719 | 0.67 | 49.0 | 21388 | 21902 |
| Human (0-48 h) | Male | 20.7 | 3.00 | 19.4 | 269 | 301 |

Concentrations are ng equivalents of $^{14}$C-labeled talarozole

Excretion of Radioactivity
In the mouse, rat and dog, over 90% recovery of the radioactive dose was achieved after oral dosing (Table 2). The radioactive dose excreted in feces ranged from 78-89% and 78-92% in male and female animals, respectively.

TABLE 2

Percent of Dose Recovered in Excreta

| Species (interval) | Sex | % in Urine | % in Feces | % in Cage Rinse | Total % Recovered |
|---|---|---|---|---|---|
| Mouse (0-48 h) | Male | 4.3 | 82.7 | 4.4 | 91.4 |
| | Female | 3.0 | 91.6 | 0.8 | 95.4 |
| Rat (0-168 h) | Male | 6.3 | 77.5 | 4.01 | 95.2 |
| | Female | 10.1 | 77.5 | 3.88 | 95.4 |
| Dog (0-192 h) | Male | 4.1 | 88.7 | 0.8 | 93.6 |
| | Female | 2.9 | 89.0 | 0.5 | 92.4 |
| Human (0-288) | Male | 7.3 | 72.2 | — | 87.7 |

It was discovered that talarozole was extensively metabolized, with the majority of metabolites excreted in the feces. In addition to uncharged drug, 17, 26 and 19 radioactive components were observed in plasma, urine, and feces from mouse, rat and dog, respectively. Unchanged $^{14}$C-labeled talarozole, M3, M4, M9 and M13 were the prominent radioactive components in mouse plasma. Rat had the greatest number of circulating metabolites in plasma. In addition to the metabolites observed in mouse, M11, M12 and M16 were observed in rat plasma. In the dog, only unchanged $^{14}$C-labeled talarozole and M4 were characterized. Unchanged $^{14}$C-labeled talarozole and M4 were the prominent metabolites in mouse feces, accounting for 6.11 and 10.56% of the dose in male mouse feces and 7.04 and 15.16% of the dose in female mouse feces. Unchanged $^{14}$C-labeled talarozole, M4, M14 and M15 were the major metabolites in rat feces, and accounted for 5.34, 4.95, 5.05 and 6.42% of the dose in male rat feces and 4.60, 7.76, 4.82 and 2.38% of the dose in female rat feces. M8 and M4 were the major metabolites in dog feces, and accounted for 11.73 and 19.88% of the dose in male dog feces and 8.86 and 17.01% of the dose in female dog feces. No unchanged $^{14}$C-labeled talarozole was detected in mouse urine. Unchanged $^{14}$C-labeled talarozole and M4 were observed as minor radio-components in rat urine, accounting for 0.07-1.90% of the dose. Two minor metabolites, M9 and M10, were identified in dog urine, accounting for 0.45-1.34% of the dose. In the human, talarozole was extensively metabolized. In addition to the unchanged talarozole, a total of seven metabolites were characterized or identified. M3 and M4 were identified as monohydroxylated talarozole. M14a and M14b were proposed as dihydroxylated talarozole. M18 and M19 were characterized as the glucuronides of dihydroxylated talarozole. The protonated molecular ion was determined for M17, but no structure could be proposed based on the available data. The major metabolic routes for ($^{14}$C)-labeled talarozole in humans were oxidation at multiple sites, followed by glucuronidation. Based on $AUC_{0-24h}$, unchanged talarozole accounted for 6.03% of the total plasma radioactivity. Three major circulating metabolites, M4, M14a, and M18, accounted for 27.8%, 12.8% and 10.7% of the total plasma radioactivity, respectively. M19 accounted for 5.60% of the total plasma radioactivity. Unchanged talarozole, M4, M14a, M18, and M19 accounted for 62.9% of the total plasma radioactivity based on $AUC_{0-24h}$ values. Metabolite M4 was a major fecal metabolite, accounting for 16% of the dose in the human feces. Unchanged talarozole and all other fecal metabolites were minor, accounting for less than 5% of the dose. Unchanged talarozole was not found in the 0 to 48 hour human urine samples and all urine metabolites accounted for <1% of the dose. Unchanged talarozole and M4 were minor radioactive components in the semen samples and M14a was a major semen metabolite.

Metabolite Characterization and Identification

Table 3 lists the talarozole metabolites characterized and/or identified by LC/MS/MS. $^{14}$C-labeled talarozole was observed to metabolize to M4 via oxidation of the benzthiazole ring, and to M3 and M13 via oxidation of the alkyl side change. Dioxidation of both the benzthiazole ring and the alkyl side chain yielded M14 and M15. Conjugation of M4 with a glucuronyl or sulfate moiety resulted in M9 and M16, respectively. Conjugation of M14 and M15 with a sulfate moiety yielded M11 and M12, respectively. Another metabolite route found only in dogs yielded the addition of 162 atomic mass units (likely, a monosaccharide) to M4 or M9 to provide M8 and M10, respectively.

Exemplary metabolic pathways of talarozole are proposed in the schematic below.

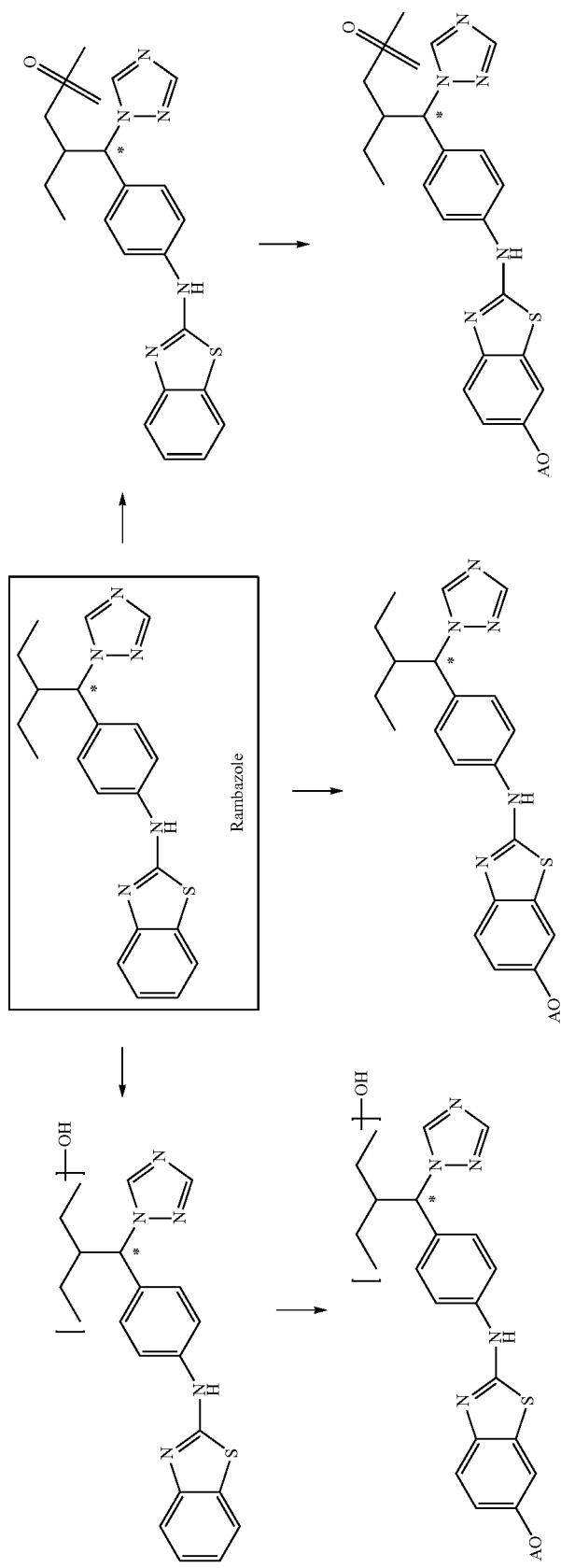
(A = H, —SO₃H, glucuronate)
*denotes position of ¹⁴C label

The proposed metabolic pathway of talarozole in humans is shown below:

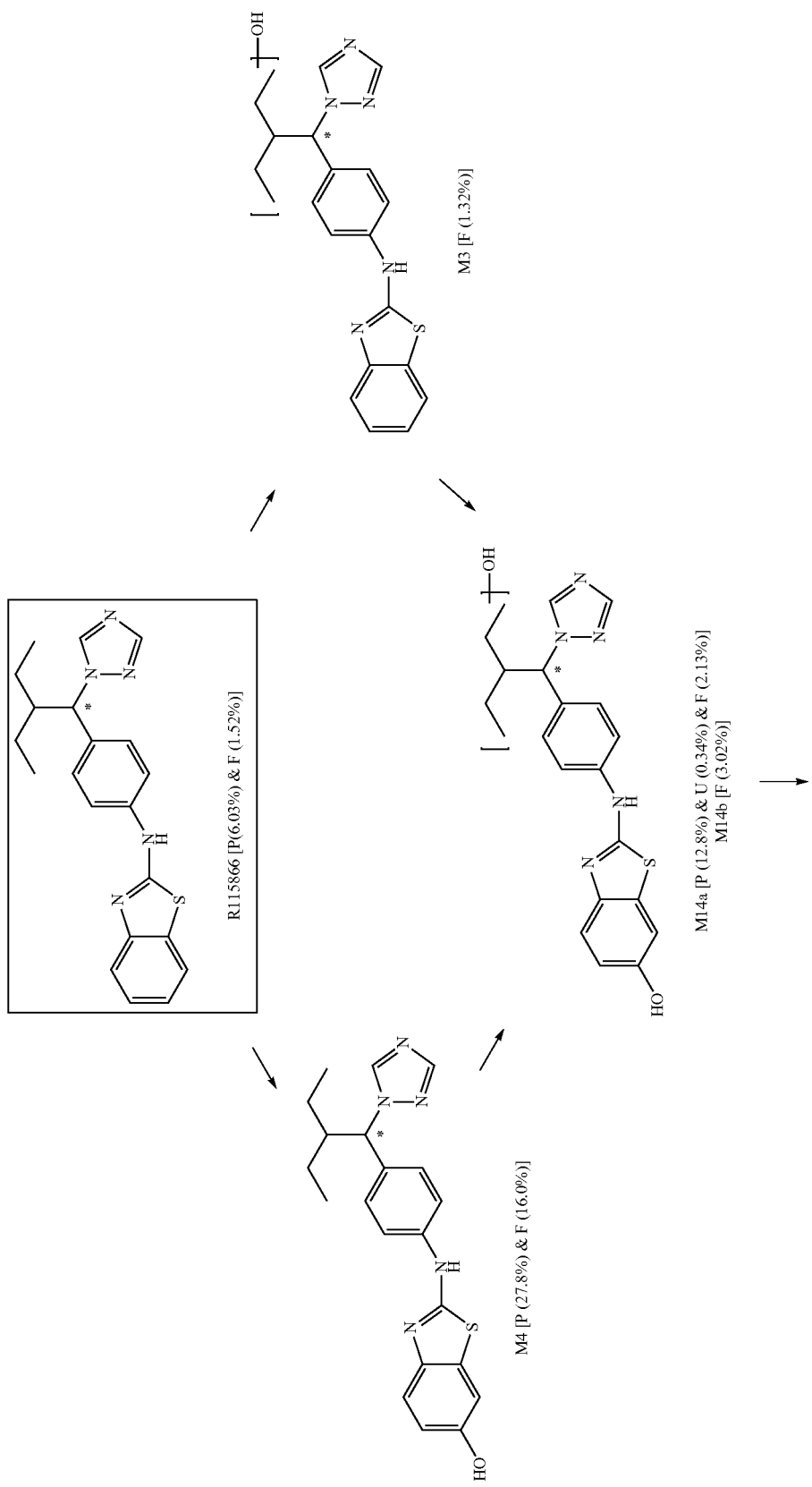

-continued
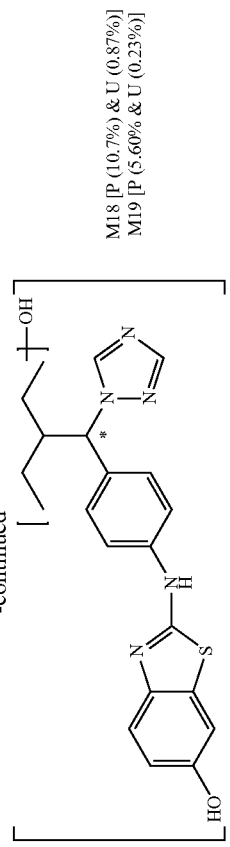
M18 [P (10.7%) & U (0.87%)]
M19 [P (5.60% & U (0.23%)]
R115866 = talarozole
*denotes position of $^{14}C$ label
P: plasma (% AUC0-24 hr); U: urine (% dose), and F: feces (% dose).

The above description is not intended to limit the claimed invention in any manner. Furthermore, the disclosed combination of features might not be absolutely necessary for the inventive solution. Disclosures of all publications, patents or published applications cited herein are incorporated by reference in their entirety.

TABLE 3

Talarozole Metabolism Comparison Across Species

| Peak Range | Metabolite Code | Proposed Structure | MW | R<sub>t</sub> (min) | Human (0.067 mg/kg)[f] ||| | Mouse (5 mg/kg)[e] |||
|---|---|---|---|---|---|---|---|---|---|---|---|
| | | | | | Plasma 0-24 h AUC (% Sample) | Urine % Dose | Feces % Dose | Semen | Plasma 0-24 h[e] AUC (% Sample) | Urine % Dose | Feces % Dose |
| | | Total Radioactivity 14C-Talarozole (Total Collection) Unidentified Metabolites from Radiochromatograms | | | 211.3 ng*hr/g (100.0%) 22 peaks 78.37 ng*hr/g (37.07%) | 7.29 19 peaks 4.84 | 80.36 26 peaks | 20 peaks | 9092.5 ng*hr/g M 66113.0 ng*hr/g F 10 peaks 4529.9 ng*hr/g (42.16%) M 2686.6 ng*hr/g (40.72%) F | 4.27 M 2.96 F 13 peaks 3.93 M 2.88 F | 82.70 M 91.59 F 16 peaks 55.97 M 56.69 F |
| 33 | Talarozole | [structure] | 377 | ~74 | 12.74 ng*hr/g (6.03%) | ND | 1.52 | X | 1377.5 ng*hr/g (15.15%) M 1420.2 ng*hr/g (21.48%) F | ND | 6.11 M 7.04 F |
| 28 | M3 | [structure] | 393 | ~60 | ND | ND | 1.32 | ND | 438.83 ng*hr/g (4.83%) M 445.29 ng*hr/g (6.73%) F | ND | ND |
| 29 | M4 | [structure] | 393 | ~62 | 58.74 ng*hr/g (27.8%) | ND | 16.00 | X | 402.45 ng*hr/g (4.43%) M 492.2 ng*hr/g (7.44%) F | 0.02 M 0.01 F Rt not confirmed | 10.56 M 15.16 F |

TABLE 3-continued

Talarozole Metabolism Across Species

| Peak Metabolite Code | Proposed Structure | MW | R$_t$ (min) | Plasma 0-24 h AUC (% Sample) | Rat (5 mg/kg)[c] Urine % Dose | Feces % Dose | Plasma 0-24 h AUC (% Sample) | Dog (5 mg/kg)[d] Urine % Dose | Feces % Dose |
|---|---|---|---|---|---|---|---|---|---|
| M8 | [structure: +162 amu bracket, benzothiazole-NH-phenyl with ethyl branched chain and triazole, HO-] | 555 | ~44 | | | | ND | | ND |
| M9 | [structure: benzothiazole with gly-O, NH-phenyl, ethyl branched chain, triazole] | 569 | ~49 | | | | 1937.3 ng*hr/g (21.31%) M 1208.2 ng*hr/g (18.27%) F | ND | ND |
| M10 | [structure: +162 amu bracket, benzothiazole with gly-O, NH-phenyl, ethyl branched chain, triazole] | 731 | ~33 | | | | | | |
| Total Radioactivity 14C-Talarozole (Total Collection) | | | | 7045.6 ng*hr/g M 8995.6 ng*hr/g F 14 peaks | 6.33 M 10.07 F 11 peaks | 77.53 M 77.57 F 22 peaks | 17047 ng*hr/g M 18225 ng*hr/g F 16 peaks | 4.13 M 2.89 F 13 peaks | 88.66 M 89.00 F 16 peaks |
| Unidentified Metabolites from Radiochromatograms | | | | 2505.2 ng*hr/g (35.56%) M 2649.7 ng*hr/g (29.45%) F | 3.47 M 5.61 F | 48.90 M 52.18 F | 9781.7 ng*hr/g (57.39%) M 7739.4 ng*hr/g (42.47%) F | 180 M 168 F | 48.95 M 43.94 F |

TABLE 3-continued

Talarozole Metabolism Comparison Across Species

| # | Name | Structure | MW | | | | | | | |
|---|---|---|---|---|---|---|---|---|---|---|
| 33 | Talarozole | benzothiazole-NH-phenyl-CH(N-triazole)-CH(ethyl)-ethyl | 377 | ~74 | 778.38 ng*hr/g (11.05%) M 3523.2 ng*hr/g (39.17%) F | 0.10 M 1.90 F | 5.34 M 4.60 F | 4132.9 ng*hr/g (24.24%) M 4228.0 ng*hr/g (23.20%) F | ND | 1.22 M 1.59 F |
| 28 | M3 | hydroxylated talarozole (–OH on alkyl) | 393 | ~60 | 429.53 ng*hr/g (6.10%) M 402.48 ng*hr/g (4.47%) F | ND | ND | | | |
| 29 | M4 | 2° hydroxylated talarozole | 393 | ~62 | 493.84 ng*hr/g (7.01%) 331.07 ng*hr/g (3.68%) F | 0.07 M 0.29 F | 4.95 M 7.76 F | 3132.4 ng*hr/g (18.37%) M 6257.6 ng*hr/g (34.33%) F | 0.04 M 0.01 F | 19.88 M 17.01 F |
| | M8 | [6-OH-benzothiazole-NH-phenyl-CH(N-triazole)-CH(ethyl)-ethyl] +162 amu | 555 | ~44 | | | | ND | ND | 11.73 M 8.86 F |

TABLE 3-continued

Talarozole Metabolism Comparison Across Species

| Peak Metabolite Range Code | Proposed Structure | MW | $R_t$ (min) | Plasma 0-24 h AUC (% Sample) | Human (0.067 mg/kg)[a] Urine % Dose | Feces % Dose | Semen | Plasma 0-24 h[e] AUC (% Sample) | Mouse (5 mg/kg)[b] Urine % Dose | Feces % Dose |
|---|---|---|---|---|---|---|---|---|---|---|
| M9 | | 569 | ~49 | 312.30 ng*hr/g (4.43%) M 1084.8 ng*hr/g (12.06%) F | ND | ND | ND | | 1.35 M 0.45 F | 4.31 M 3.09 F |
| M10 | +162 amu [gly-O ... gly-O] | 731 | ~33 | | | | | | 0.84 M 0.64 F | ND |
| M11 | | 489 | ~36 | | | | | | | |
| M12 | | 487 | ~41 | | | | | | | |

TABLE 3-continued

Talarozole Metabolism Comparison Across Species

| | | | | | | | |
|---|---|---|---|---|---|---|---|
| M13 | [structure: benzothiazole-NH-phenyl with triazole and ketone substituent] | 391 | ~67 | | | 406.52 ng*hr/g (4.47%) M 360.47 ng*hr/g (5.45%) F | ND | ND |
| 14 M14a | [structure: 6-hydroxybenzothiazole-NH-phenyl with triazole and hydroxyl chain] | 409 | ~42 | 27.10 ng*hr/g (12.83%) | 0.34 | 2.14 | X |
| 15 M14b | [structure: 6-hydroxybenzothiazole-NH-phenyl with triazole] | 409 | ~44 | ND | ND | 3.02 | X |
| M15 | [structure: 6-hydroxybenzothiazole-NH-phenyl with triazole and ketone] | 407 | ~55 | | | | |
| M16 | [structure: 6-sulfobenzothiazole-NH-phenyl with triazole] | 473 | ~55 | | | | |

TABLE 3-continued

Talarozole Metabolism Across Species

| Peak Range | Metabolite Code | Proposed Structure | MW | R_t (min) | Plasma 0-24 h AUC (% Sample) | Rat (5 mg/kg)[c] Urine % Dose | Feces % Dose | Plasma 0-24 h AUC (% Sample) | Dog (5 mg/kg)[d] Urine % Dose | Feces % Dose |
|---|---|---|---|---|---|---|---|---|---|---|
| 31 | M17 | [structure: +46 Da, HO-, triazole, benzothiazole-NH, OH] | 439 | ~68 | ND | ND | 2.38 | ND | | |
| 7 | M18 | [structure with -OH, triazole, benzothiazole-NH-OH] | 585 | ~34 | 22.52 ng*hr/g (10.66%) | 0.87 | ND | ND | | |
| 9 | M19 | [structure with gly, -OH, triazole, benzothiazole-NH-OH] | 585 | ~36 | 11.83 ng*hr/g (5.60%) | 0.23 | ND | ND | | |
| | M11 | [structure with -OH, triazole, benzothiazole-NH, HO_3SO-] | 489 | ~36 | 1177.6 ng*hr/g (16.71%) M 298.32 ng*hr/g (3.32%) F | ND | ND | | | |

TABLE 3-continued

Talarozole Metabolism Comparison Across Species

| | Structure | m/z | | | |
|---|---|---|---|---|---|
| M12 | (benzothiazole-NH-phenyl with HO₃SO group, triazole, ethyl, aldehyde) | 487 | ~41 | 583.62 ng*hr/g (8.28%) M 268.42 ng*hr/g (2.98%) F | ND | ND |
| M13 | (benzothiazole-NH-phenyl, triazole, ethyl, ketone with gem-dimethyl) | 391 | ~67 | 557.70 ng*hr/g (7.92%) M 219.16 ng*hr/g (2.44%) F | ND | ND |
| 14 M14a | (benzothiazole-OH-NH-phenyl, triazole, ethyl, OH) | 409 | ~42 | ND | ND | 5.05 M 4.82 F |
| 15 M14b | | 409 | ~44 | | | |
| M15 | (benzothiazole-OH-NH-phenyl, triazole, ethyl, ketone) | 407 | ~55 | ND | ND | 6.42 M 2.38 F |

TABLE 3-continued

Talarozole Metabolism Comparison Across Species

| | | | | | |
|---|---|---|---|---|---|
| M16 | | 473 | ~55 | 207.48 ng*hr/g (2.94%) M 218.47 ng*hr/g (2.43%) F | 0.16 M 0.31 F Rt not confirmed | 1.42 M 1.33 F Rt not confirmed |
| 31 M17 | | 439 | ~68 | | | |
| 7 M18 | | 585 | ~34 | | | |
| 9 M19 | | 585 | ~36 | | | |

I claim:

1. A method of treating a keratinization-associated disorder of the skin, hair, or nail in a mammal in need thereof, comprising administering to said mammal an effective amount of a compound of Formula I or a pharmaceutically acceptable salt thereof:

Formula I

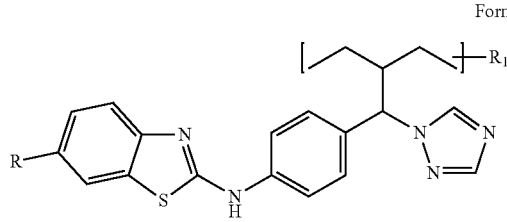

wherein

R is H, OH, OSO₃H or O-glucuronate;

R₁ is H, OH, OSO₃H, O-glucuronate or =O;

or a pharmaceutically acceptable salt thereof, with the proviso that when R=H, R₁ cannot also be H.

2. The method according to claim 1 wherein the keratinization-associated disorder is psoriasis, acne, actinic keratosis, eczema, rosacea, ichthyosis, alopecia or photodamaged skin.

3. The method according to claim 1 wherein the keratinization-associated disorder is ichthyosis.

4. The method according to claim 1, wherein the compound is selected from the group consisting of

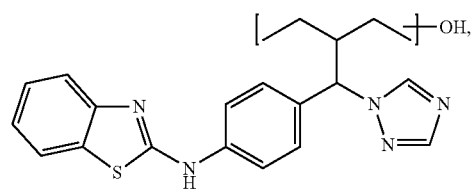

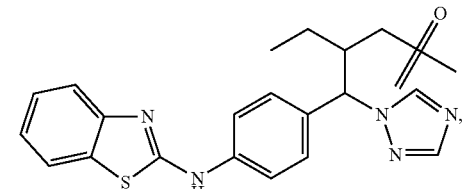

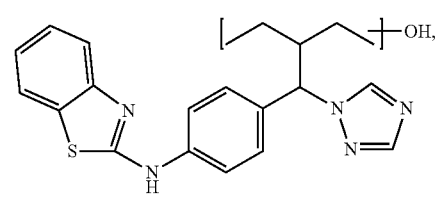

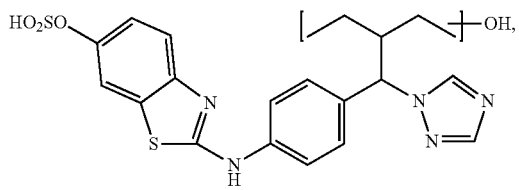

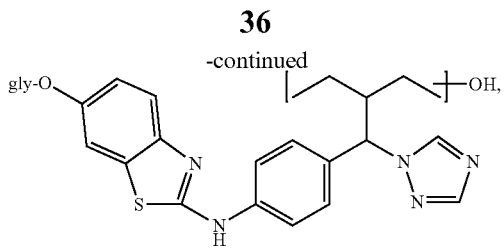

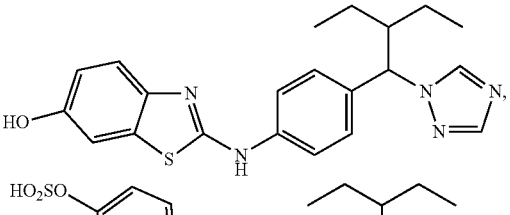

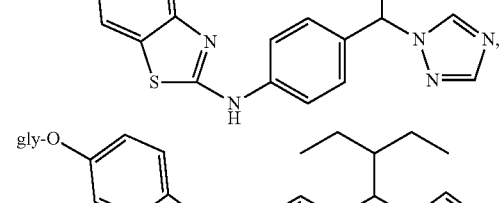

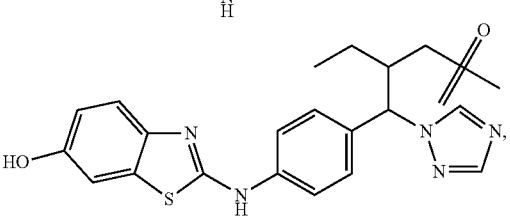

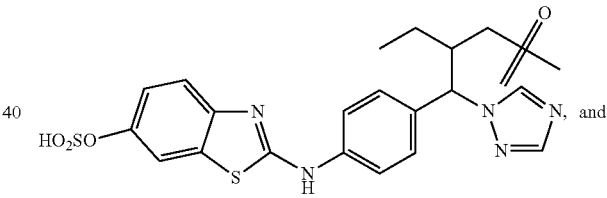

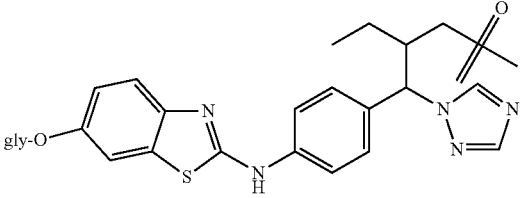

wherein gly is glucuronate, or a pharmaceutically acceptable salt thereof.

5. The method according to claim 1 wherein the compound is

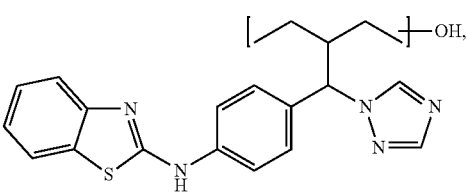

or a pharmaceutically acceptable salt thereof.

6. The method according to claim 1 wherein the compound is

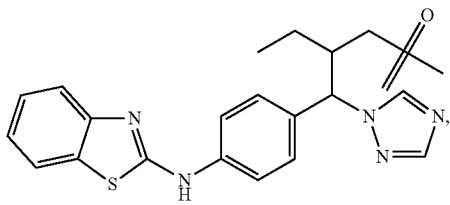

or a pharmaceutically acceptable salt thereof.

7. The method according to claim 1 wherein the compound is

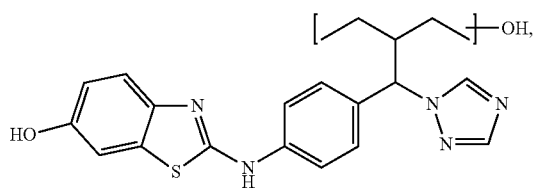

or a pharmaceutically acceptable salt thereof.

8. The method according to claim 1 wherein the compound is

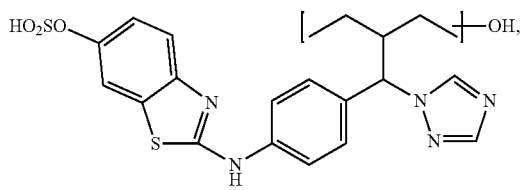

or a pharmaceutically acceptable salt thereof.

9. The method according to claim 1 wherein the compound is

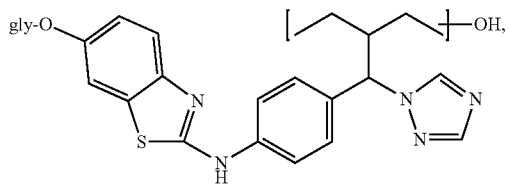

or a pharmaceutically acceptable salt thereof.

10. The method according to claim 1 wherein the compound is

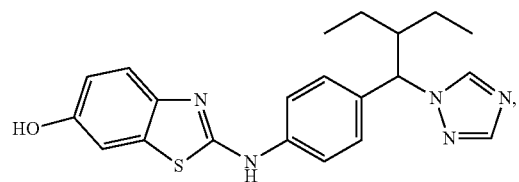 [SMILES: CCC(CC)C(c1ccc(Nc2nc3ccc(O)cc3s2)cc1)n1cncn1]

or a pharmaceutically acceptable salt thereof.

11. The method according to claim 1 wherein the compound is

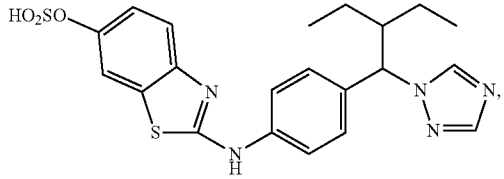

or a pharmaceutically acceptable salt thereof.

12. The method according to claim 1 wherein the compound is

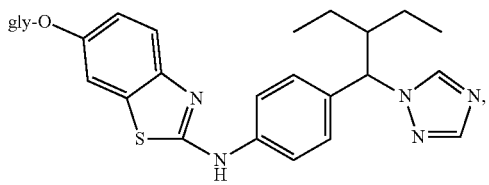

or a pharmaceutically acceptable salt thereof.

13. The method according to claim 1 wherein the compound is

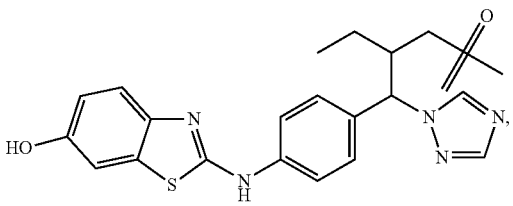

or a pharmaceutically acceptable salt thereof.

14. The method according to claim 1 wherein the compound is

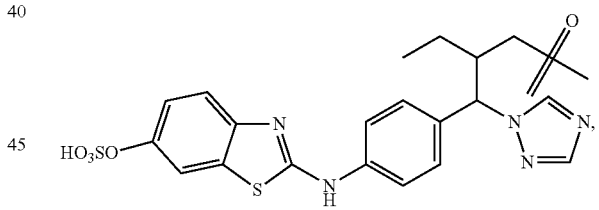

or a pharmaceutically acceptable salt thereof.

15. The method according to claim 1 wherein the compound is

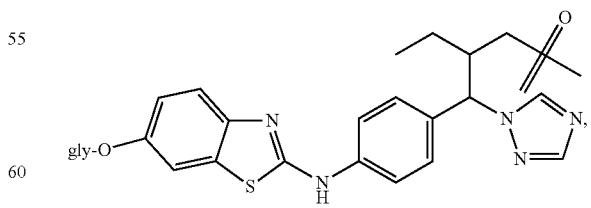

or a pharmaceutically acceptable salt thereof.

16. The method according to claim 1 wherein the mammal is a human.

* * * * *